United States Patent
Badawy et al.

(10) Patent No.: US 9,452,134 B2
(45) Date of Patent: Sep. 27, 2016

(54) APIXABAN SOLUTION FORMULATIONS (71) Applicant: Bristol-Myers Squibb Company, Princeton, NJ (US)

(72) Inventors: Sherif Ibrahim Farag Badawy, Dayton, NJ (US); Susan Lum, Toronto (CA)

(73) Assignees: Bristol-Myers Squibb Company, Princeton, NJ (US); Pfizer Inc., New York, NY (US)

( * ) Notice: Subject to any disclaimer, the term of this patent is extended or adjusted under 35 U.S.C. 154(b) by 0 days.

(21) Appl. No.: 14/430,275

(22) PCT Filed: Sep. 26, 2013

(86) PCT No.: PCT/US2013/062051
§ 371 (c)(1),
(2) Date: Mar. 23, 2015

(87) PCT Pub. No.: WO2014/052678
PCT Pub. Date: Apr. 3, 2014

(65) Prior Publication Data
US 2015/0224053 A1 Aug. 13, 2015

Related U.S. Application Data (60) Provisional application No. 61/705,943, filed on Sep. 26, 2012, provisional application No. 61/773,032, filed on Mar. 5, 2013.

(51) Int. Cl.
*A61K 31/44* (2006.01)
*A61K 9/08* (2006.01)
*A61K 31/4545* (2006.01)
*A61K 47/10* (2006.01)
*A61K 47/20* (2006.01)
*A61K 47/26* (2006.01)
*A61K 47/32* (2006.01)

(52) U.S. Cl.
CPC ............. *A61K 9/08* (2013.01); *A61K 31/4545* (2013.01); *A61K 47/10* (2013.01); *A61K 47/20* (2013.01); *A61K 47/26* (2013.01); *A61K 47/32* (2013.01)

(58) Field of Classification Search
CPC .. A61K 31/4545; A61K 47/10; A61K 47/20; A61K 47/26; A61K 47/32; A61K 9/08
See application file for complete search history.

(56) References Cited

U.S. PATENT DOCUMENTS

| 6,967,208 | B2 | 11/2005 | Pinto et al. |
| 2012/0087978 | A1 | 4/2012 | Nause |
| 2013/0045245 | A1 | 2/2013 | Patel et al. |

FOREIGN PATENT DOCUMENTS

| WO | 2007/022165 A2 | 2/2007 | |
| WO | WO 2007022165 A2 * | 2/2007 | ........... A61K 9/0019 |
| WO | 2010/147978 A1 | 12/2010 | |
| WO | WO 2010147978 A1 * | 12/2010 | ........... A61K 9/0004 |
| WO | 2011/106478 A2 | 9/2011 | |

OTHER PUBLICATIONS http://www.swrcb.ca.gov/losangeles/board_decisions/adopted_orders/WDR_Update/Benzenesulfonicacid,sodiumsulfosuccinate,xanthangum,guargum-Surfactants.pdf, accessed on Aug. 10, 2015.*
Preliminary Search Report with Opinion on Patentability (dated Mar. 18, 2016).

* cited by examiner

*Primary Examiner* — Jean Cornet
(74) *Attorney, Agent, or Firm* — Fitzpatrick, Cella, Harper & Scinto (57) ABSTRACT

Apixaban liquid formulation is provided. Also provided is a method of administering an apixaban liquid formulation.

15 Claims, 7 Drawing Sheets

Fig. 1A

Taste Assessment Method

- Open-label studies enrolling 4–5 trained professional adult sensory panelists. Panelists provided written informed consent, were generally healthy, and had no contraindications to tasting apixaban.
- All subjects tasted the same treatment sample simultaneously. Each sample was held in the mouth for approximately 10 seconds to provide time for evaluation, and then the sample was expectorated (swish-and-spit).
- Initial flavor and mouthfeel attributes and aftertaste attributes were recorded.
- Between samples, the subjects cleansed their palates using water and unsalted crackers. A minimum 10-minute washout period was provided between samples.
- The study protocols were approved by an appropriate Independent Review Board.
- Physical assessment (medical history, physical examination, pregnancy test in women) was conducted at screening.
- All subjects were monitored for adverse events.
- Multiple preservatives, sweeteners, and flavors were evaluated in the taste assessments.

Flavor Profile Method
- The study samples were evaluated using the Flavor Profile Method3 of descriptive sensory analysis. Flavor Profile is used to identify, characterize, and quantify the sensory attributes of products, e.g., basic tastes, aroma, texture, and mouthfeel.
- Chemical reference standards were used to establish the intensity scale and maintain panelist calibration.

Flavor Profile Definitions
- Amplitude: Initial overall perception of balance and fullness. Measured in flavored formulations.
- Amplitude Scale:
  - 0 = None
  - 1 = Low
  - 2 = Moderate
  - 3 = High
- Character Notes: Aromatics, basic tastes, and feeling factors (listed in order of appearance along with a measurement of intensity).
- Intensity Scale:
  - 0 = None
  - 1 = Slight
  - 2 = Moderate
  - 3 = Strong
- Aftertaste: Measurement of all sensation remaining at 1, 3, 5, and 10 minutes.

Fig. 1B

Flavor Profile Interpretation
- The Flavor Leadership Criteria used to interpret sensory results and guide the development of products that can be differentiated on the basis of perceived flavor quality.

Flavor Leadership Criteria
- Immediate impact of the identifying flavor, eg, orange, berry, mint
- Rapid development of balanced, full flavor, as measured by Amplitude
- Compatible mouthfeel factors, eg, minimal trigeminal irritation
- No "off" flavors, eg, bitterness, trigeminal irritation, aversive aromatics
- Short (or appropriate) aftertaste, eg, sufficient duration to cover aversive attributes Amplitude Scoring
- At the end of the taste evaluation an amplitude score was provided on a scale of 0–3.
- Target amplitude for palatable pharmaceutical product is 1 ½ (1–2 is deemed acceptable).
- The target amplitude score should be high enough so that the product is acceptable to patients, while not so high that the product may pose a risk for overdose.
- Additional goals include reducing the aversive attributes of the excipient system, specifically the aromatic off-notes (oxidized oil, woody/nonenal, bitterness, and mouthfeels).

Fig. 2A

Results of Taste Assessment Method

- The final excipients were selected based on both functional performance and sensory performance.

Sensory-Directed Excipient Selection

| | Excipient Evaluated | Included in Final Formulation |
|---|---|---|
| Preservatives | Parabens | Parabens |
| ↓ | Benzoic acid | |
| Sweeteners | Nutritive: sucrose, fructose, high-fructose corn syrup | Fructose |
| ↓ | High intensity: sucralose, sodium saccharin, acesulfame potassium (Ace-K) | Sucralose |
| Flavors | Orange, cherry, grape, fruit punch | Orange |

- The flavor profile of the unflavored and optimized (flavored) oral liquid formulation are presented in the table below. The improvement of the flavor profile is also presented.

Flavor Profile: Unflavored Apixaban and Orange-Flavored Apixaban Oral Liquid Formulation

| | Initial | | 1 Min | | 3 Min | | 5 Min | | 10 Min | |
|---|---|---|---|---|---|---|---|---|---|---|
| | Starting Base | Optimized Formulation | Starting Base | Optimized Formulation | Starting Base | Optimized Formulation | Starting Base | Optimized Formulation | Starting Base | Optimized Formulation |
| Amplitude | NA | 1-1½ | — | — | — | — | — | — | — | — |
| Sweet | 2 | 2½ | 1 | 2 | ½ | 1½ | — | 1 | — | ½ |
| Juicy orange aromatic | — | 1½ | — | 1 | — | ½ | — | ½ | — | — |
| Oxidized oil aromatic | 2 | — | 1 | — | — | — | — | — | — | — |
| Sour | — | 1 | — | — | — | — | — | — | — | — |
| Woody/nonenal aromatic | 2 | 1 | 2 | ½ | 1½ | ½ | 1 | — | ½ | — |
| Oily mouthfeel | 2 | 1½ | 1½ | 1 | 1 | — | ½ | — | — | — |
| Bitter | 1½ | — | 1 | — | 1 | — | ½ | — | ½ | — |
| Vanillin | — | ½ | — | — | — | — | — | — | v | — |
| Warming | 1½ | 1 | 1 | — | — | — | — | — | — | — |
| Tongue sting | 1 | — | 1 | ½ | 1 | ½ | ½ | — | ½ | — |
| Numbing | — | ½ | 1 | ½ | 1 | ½ | — | — | — | — |
| Drying | — | — | — | — | — | ½ | 1 | ½ | 1 | ½ |

Abbreviation: NA, not available.

Fig. 2B

Flavor Leadership Interpretation

| 1. Aromatic Identity | 2. Amplitude | 3. Mouthfeel | 4. Off-Notes | 5. Aftertaste |
|---|---|---|---|---|
| Juicy orange aromatics appear early with underlying vanillin notes | The optimized formulation had a low-to-moderate level of balance and fullness (Amplitude) appropriate for oral drug products | The flavor system reduced the oily, warming, numbing, tongue sting and dry mouthfeels | The flavor system effectively eliminated bitterness and oxidized oil aromatics and reduced the woody/ nonenal aromatics | In the optimized formulation, orange aromatics and sweetness linger into the aftertaste, providing coverage of the off-notes |

- The flavor quality (Amplitude and coverage of aversive sensory attributes) of apixaban liquid formulation was largely unchanged after 1- and 2-year storage periods, as measured by the trained adult sensory panelists. The flavor profile at 2 years postmanufacture is presented in the table below.

Flavor Profile: Orange-Flavored Apixaban CTM Oral Liquid Formulation (Two Years Postmanufacture)

|  | Initial | 1 Min | 3 Min | 5 Min | 10 Min |
|---|---|---|---|---|---|
| Amplitude | 1 | -- | -- | -- | -- |
| Sweet | 2 | 2½ | 1½ | 1 | ½ |
| Oxidized Oil/nonenal | 1½ | 1½ | 1 | 1 | ½ |
| Candied orange aromatic | 1½ | 1 | 1 | ½ | ½ |
| Oily mouthfeel | 1½ | 1 | ½ | -- | -- |
| Sour | 1 | ½ | -- | -- | -- |
| Warming | 1 | ½ | -- | -- | -- |
| Tongue sting | ½ | ½ | ½ | ½ | ½ |
| Numbing | -- | ½ | ½ | ½ | -- |
| Drying | -- | -- | ½ | 1 | ½ |

Abbreviation: CTM, Clinical Trial Material.

Fig. 3

Study 1: Mean apixaban plasma concentration-time profile (error bars show +1 standard deviation).

A = apixaban 2 x 5 mg Phase 3 tablets

B = apixaban 25 mL x 0.4 mg/mL liquid formulation

Fig. 4

Study 2: Mean apixaban plasma concentration-time profile (error bars show +1 standard deviation).

A = Single dose apixaban 5 mg (12.5 ml) liquid formulation administered by mouth via oral syringe B = Single dose apixaban 5 mg (12.5 ml) liquid formulation administered via NGT immediately followed by 60 mL of $D_5W$ via NGT C = Single dose apixaban 5 mg (12.5 ml) liquid formulation administered via NGT immediately followed by 60 mL of infant formula via NGT

APIXABAN SOLUTION FORMULATIONS

CROSS-REFERENCE TO RELATED APPLICATIONS

This application claims priority under 35 U.S. C. §119(e) to U.S. provisional patent Application No. 61/705,943, filed Sep. 26, 2012, and U.S. provisional patent Application No. 61/773,032, filed Mar. 5, 2013; the entire contents of these applications are incorporated herein by reference.

FIELD OF THE INVENTION

This invention relates to apixaban pharmaceutical formulations. In particular, it relates to apixaban liquid formulations.

BACKGROUND OF THE INVENTION

Apixaban is a known compound having the structure:

The chemical name for apixaban is 4,5,6,7-tetrahydro-1-(4-methoxyphenyl)-7-oxo-6-[4-(2-oxo-1-piperidinyl)phenyl]-1H-pyrazolo[3,4-c]pyridine-3-carboxamide (CAS name) or 1-(4-methoxyphenyl)-7-oxo-6-[4-(2-oxo-1-piperidinyl)phenyl]-4,5,6,7-tetrahydro-1H-pyrazolo[3,4-c]pyridine-3-carboxamide (IUPAC name).

Apixaban is disclosed in U.S. Pat. No. 6,967,208 and in U.S. Patent Application Publication Nos. 2012/0087978 and 2013/0045245, which are all herein incorporated by reference in their entirety. Apixaban has utility as a Factor Xa inhibitor, and is being developed for oral administration in a variety of indications that require the use of an antithrombotic agent, such as in patients following elective hip or knee surgery and stroke prevention in atrial fibrillation or for treatment of venous thrombosis.

A liquid formulation is important for administration of apixaban in the pediatric population and adults who are unable to swallow a solid dosage form.

SUMMARY OF THE INVENTION

Disclosed herein is a liquid formulation comprising apixaban and a vehicle. The solubility of apixaban in this vehicle can be at least 0.50 mg/mL.

The vehicle can comprise water and at least two solubilizers selected from the group consisting of a non-ionic surfactant, an ionic surfactant, a hydrophilic polymer, ethanol, a polyhydric alcohol, a polyethylene glycol, and a carbohydrate.

In an embodiment of the present invention, the liquid formulation is suitable for oral administration and/or administration through a nasogastric tube and/or gastronomy tube using a dosing syringe.

Another embodiment of the present invention is a method for treating a thromboembolic disorder, comprising administering to a patient in need thereof a therapeutically effective amount of the liquid formulation comprising apixaban and a vehicle.

BRIEF DESCRIPTION OF THE DRAWINGS

FIGS. 1A and 1B describe a taste assessment method in Example 5.

DETAILED DESCRIPTION OF THE INVENTION

Low aqueous solubility of apixaban (0.04 mg/mL) is a major hurdle to the development of a liquid formulation of apixaban. Extensive solubility studies were conducted to identify a vehicle that supports a low dose concentration.

It was determined that a concentration of 0.4 mg/mL of apixaban in an oral liquid formulation adequately supports a desired dosage range of 0.04 mg to 5.0 mg with acceptable volumes ranging, for example, between 0.10 mL and 12.5 mL, which can be accurately measured and conveniently administered in the target patient population. Extensive solubility studies were conducted to identify a vehicle that supports the 0.4 mg/mL concentration. A minimum solubility of apixaban of at least 0.50 mg/mL at room temperature (15-25° C.) can provide a robust formulation at the 0.4 mg/mL target concentration. Since it is preferable for the apixaban oral liquid formulation in accordance with the present invention to be suitable for ambient storage, this solubility helps to maintain apixaban in a dissolved state within the range of temperatures to which the formulation may be exposed during shipping and handling by the patients.

Co-solvents and surfactants were evaluated as solubilizers to determine if the above-noted target solubility of apixaban can be achieved. In particular, solubilizers acceptable for use in pharmaceutical products were evaluated. In addition, the concentration of a given solubilizer in the formulation preferably did not exceed acceptable daily intake of the excipient per regulatory guidelines and excipient safety literature.

Numerous combinations of co-solvents and surfactants were evaluated but did not provide the desired solubility. Reference Examples 1-4 are a few of the vehicles tested with combinations of surfactants and co-solvents that did not result in the solubility of apixaban in the vehicle of at least 0.50 mg/mL. These Reference Examples are summarized in Table 3.

It has now been determined that particular solubilizers and/or surfactants are preferred for a vehicle that provides the solubility of apixaban in the vehicle of at least 0.50 mg/mL. This preferred vehicle comprises water and at least two solubilizers selected from the group consisting of non-ionic surfactant, ionic surfactant, hydrophilic polymer, ethanol, polyhydric alcohol, polyethylene glycol, and carbohydrate. The above phrase "at least two solubilizers" means that, for example, there can be a non-ionic surfactant and a hydrophilic polymer, but it also means that for example, two different ionic surfactants comply with the phrase "at least two solubilizers". Accordingly, at least two non-ionic surfactants, at least two ionic surfactants, at least two hydrophilic polymers, at least two polyhydric alcohols, at least two polyethylene glycols, and/or at least two carbohydrates may be used as at least two such solubilizers. Preferably, the vehicle includes more than one type of solubilizer.

Accordingly, the liquid formulation preferably includes apixaban and a vehicle, which includes water and at least two solubilizers selected form the group consisting of a non-ionic surfactant, an ionic surfactant, a hydrophilic polymer, ethanol, a polyhydric alcohol, a polyethylene glycol, and a carbohydrate, and the solubility of apixaban in the vehicle is at least 0.50 mg/mL. More preferably, the solubility of apixaban in the vehicle is at least 0.51 mg/mL; even more preferably, at least 0.52 mg/mL; even more preferably, at least 0.53 mg/mL; even more preferably, at least 0.54 mg/mL; even more preferably, at least 0.55 mg/mL; even more preferably, at least 0.56 mg/mL; even more preferably, at least 0.57 mg/mL; even more preferably, at least 0.58 mg/mL, even more preferably, at least 0.59 mg/mL, and even more preferably, at least 0.60 mg/mL at room temperature (15-25° C.).

The solubility of apixaban in the vehicle may be, for example, from about 0.60 mg/mL to about 0.8 mg/mL, from about 0.60 mg/mL to about 0.75 mg/mL, or from about 0.70 mg/mL to about 0.74 mg/mL.

Preferably, at least 90 wt %; more preferably, at least 91 wt %; even more preferably, at least 92%; even more preferably, at least 93%; even more preferably, at least 94 wt %; even more preferably, at least 95 wt %; even more preferably, at least 96 wt %; even more preferably, at least 97 wt %; even more preferably, at least 98 wt %; even more preferably, at least 99 wt %; even more preferably, at least 99.5 wt %; and even more preferably, 100 wt % of apixaban present in the liquid formulation is dissolved in the vehicle.

Solubility of apixaban can be measured by known methods. For example, solubility can be measured by mixing excess apixaban with the vehicle for sufficient time until the concentration of apixaban in a filtered sample of the vehicle reaches equilibrium concentration and does not show further change with time. Such equilibrium concentration represents the solubility of apixaban in the vehicle as referred to herein.

In an embodiment of the present invention, water content of the vehicle is about 20% w/w to about 30% w/w, more preferably, about 23% w/w to about 27% w/w, even more preferably, about 23.5% w/w to about 26% w/w of the vehicle; non-ionic surfactant content of the vehicle is about 11% w/w to about 14% w/w, more preferably, 11.5% w/w to about 13.5% w/w, even more preferably, about 12% w/w to about 13% w/w of the vehicle; ionic surfactant content of the vehicle is 0% w/w to about 1% w/w, more preferably, about 0.2% w/w to about 0.8% w/w, even more preferably, about 0.4% w/w to about 0.6% w/w of the vehicle; hydrophilic polymer content of the vehicle is about 1% w/w to about 6% w/w, more preferably, about 2% w/w to about 5% w/w, even more preferably, about 2.2% w/w to about 4.2% w/w of the vehicle; polyhydric alcohol content of the vehicle is about 31% w/w to about 37% w/w, more preferably, about 32% w/w to about 36% w/w, even more preferably, about 33% w/w to about 35% w/w of the vehicle; polyethylene glycol content of the vehicle is about 4% w/w to about 6% w/w, more preferably, about 4.5% w/w to about 5.5% w/w, even more preferably, about 4.8% w/w to about 5.2% w/w of the vehicle; and carbohydrate content of the vehicle is about 18% w/w to about 22% w/w, more preferably, about 19% w/w to about 21% w/w, even more preferably, about 19.8% w/w to about 20.2% w/w of the vehicle.

Preferably, the vehicle contains two or more solubilizers selected from the following: a non-ionic surfactant, an ionic surfactant, a hydrophilic polymer, ethanol, a polyhydric alcohol, a polyethylene glycol, and a carbohydrate.

A non-ionic surfactant as referred to herein is a non-ionizable surface-active agent which reduces the surface tension of a liquid and thus allows it to foam or wet a solid. Non-limiting examples of non-ionic surfactants that can be used in the apixaban liquid formulation are polyoxyethylene sorbitan fatty acid esters (polysorbates), poloxamers, polyoxyethylene castor oil derivatives, polyoxyglycerides, vitamin E polyethylene glycol succinate, and macrogol 15 hydroxystearate. Non-limiting examples of polysorbates are polysorbate 20, polysorbate 40, polysorbate 60, and polysorbate 80. Non-limiting examples of poloxamers are poloxamer 124, poloxamer 188, poloxamer 237, poloxamer 338, and poloxamer 407. Non-limiting examples of polyoxyethylene castor oil derivatives are polyoxyl 35 castor oil and polyoxyl 40 hydrogenated castor oil. Non-limiting examples of polyoxyglycerides are polyethylene glycol-8 caprylic/capric glycerides.

An ionic surfactant as referred to herein is a surface-active agent with ionizable group(s) which reduces the surface tension of a liquid and thus allows it to foam or wet a solid. Non-limiting examples of ionic surfactants that can be used in the apixaban liquid formulation are sodium lauryl sulfate and docusate sodium.

A hydrophilic polymer as referred to herein is a compound of high molecular weight derived by the addition of many smaller units and which has a strong affinity for water. Non-limiting examples of hydrophilic polymers that can be used in the apixaban liquid formulation are povidone (e.g., Povidone K25 or 29/32), copovidone, hydroxypropyl cellulose, and hydroxypropyl methylcellulose.

A polyhydric alcohol as referred to herein is a compound with more than one hydroxyl group. Non-limiting examples of polyhydric alcohols that can be used in the apixaban liquid formulation are glycerin, propylene glycol, sorbitol, and mannitol.

A polyethylene glycol as referred to herein is a polymer of ethylene glycol formed by the reaction of ethylene oxide and water. Non-limiting examples of polyethylene glycols that can be used in the apixaban liquid formulation are polyethylene glycol 200, polyethylene glycol 300, and polyethylene glycol 400.

A carbohydrate as referred to herein is a class of organic compounds that are polyhydroxy aldehydes or polyhydroxy ketones. Non-limiting examples of carbohydrates that can be used in the apixaban liquid formulation are fructose, sucrose, and lactose.

In another embodiment of the present invention, the vehicle of the liquid formulation comprises: glycerin, at 0% w/w to about 30% w/w, more preferably, about 15% w/w to about 25% w/w of the vehicle; propylene glycol, at 0% w/w to about 20% w/w, more preferably, about 7% w/w to about 20% w/w of the vehicle; polyethylene glycol, at 0% w/w to about 20% w/w, more preferably, about 2% w/w to about 7% w/w of the vehicle; polysorbate, at 0% w/w to about 20% w/w, more preferably, about 5% w/w to about 18% w/w of the vehicle; povidone, at 0% w/w to about 7% w/w, more preferably, about 2% w/w to about 5% w/w of the vehicle; sorbitol, at 0% w/w to about 30% w/w, more preferably, about 15% w/w to about 25% w/w of the vehicle; sodium lauryl sulfate, at 0% to about 2%, more preferably, about 0.25% w/w to about 1% w/w of the vehicle; copovidone, at 0% w/w to about 7% w/w, more preferably, about 2% w/w to about 5% w/w of the vehicle; poloxamer, at 0% w/w to about 7% w/w, more preferably, about 2% w/w to about 7% w/w of the vehicle; fructose, at 0% w/w to about 30% w/w, more preferably, about 15% w/w to about 25% w/w of the vehicle, and sucrose, at 0% w/w to about 30% w/w, more preferably, about 15% w/w to about 25% w/w of the vehicle.

In an embodiment of the present invention, the vehicle of the liquid formulation comprises: glycerin, at about 20% w/w of the vehicle; propylene glycol, at about 14% w/w of the vehicle, polyethylene glycol 400, at about 5% w/w of the vehicle; and polysorbate 80, at about 12.5% w/w of the vehicle.

Preferred solubilizers and their preferred concentration ranges are shown in Table 1.

TABLE 1

Preferred solubilizers and concentration ranges in vehicle (w/w of the vehicle)

| Solubilizer | % w/w |
| --- | --- |
| Glycerine | 0-30 |
| Propylene glycol | 0-20 |
| Polyethylene Glycol 300 or 400 | 0-20 |
| Polysorbate 20, 40, 60, or 80 | 0-20 |
| Povidone K25 or 29/32 | 0-7 |
| Sorbitol | 0-30 |
| Sodium lauryl sulfate | 0-2 |
| Copovidone | 0-7 |
| Poloxamer | 0-7 |
| Fructose | 0-30 |
| Sucrose | 0-30 |

More preferred concentration ranges for these solubilizers are shown in Table 2.

TABLE 2

More preferred concentration ranges in vehicle (w/w of the vehicle)

| Solubilizers | % w/w |
| --- | --- |
| Glycerine | 15-25 |
| Propylene glycol | 7-20 |
| Polyethylene Glycol 300 or 400 | 2-7 |
| Polysorbate 20, 40, 60, or 80 | 5-18 |
| Povidone K25 or 29/32 | 2-5 |
| Sorbitol | 15-25 |
| Sodium lauryl sulfate | 0.25-1 |
| Copovidone | 2-5 |
| Poloxamer | 2-7 |
| Fructose | 15-25 |
| Sucrose | 15-25 |

In an embodiment of the present invention, the liquid formulation comprises: apixaban, at about 0.034% w/w of the liquid formulation; glycerin, at about 20% w/w of the liquid formulation; propylene glycol, at about 14% w/w of the liquid formulation; polyethylene glycol 400, at about 5% w/w of the liquid formulation; polysorbate 80, at about 12.5% w/w of the liquid formulation; povidone K25, at about 4% w/w of the liquid formulation; sodium lauryl sulfate, at about 0.5 w/w of the liquid formulation; and fructose, at about 20% % w/w of the liquid formulation.

A liquid formulation in accordance with the present invention may also include a flavoring agent, a sweetener, a preservative, a buffer, or any combination thereof. Non-limiting examples of flavoring agents are orange flavor (commercially available as Ungerer #FN924), cherry, strawberry, bubblegum, grape, and fruit punch flavors. Non-limiting examples of sweeteners are sucralose, aspartame, acesulfame potassium, saccharin sodium, sucrose, fructose, and high fructose corn syrup. Non-limiting examples of preservatives are methylparaben, ethylparaben, propylparaben, benzoic acid, and sorbic acid. Non-limiting examples of buffers are citrate buffer, acetate buffer, and phosphate buffer.

In an embodiment of the present invention, the liquid formulation is suitable for oral administration. Alternatively, or in addition, the liquid formulation is suitable for administration through a nasogastric tube (NGT) and/or through a gastronomy tube (G-tube) using a dosing syringe. In clinical situations, Dextrose 5% (D5W) may be used to flush NGT in infants who do not have fluid restriction, while infant formula may be used in infants who have fluid restriction. For adults who cannot swallow a solid dosage form, enteral meal may be administered.

Preferably, the apixaban liquid formulation provides similar bioavailability and pharmacokinetic properties to Eliquis® (apixaban) tablets. For instance, the apixaban liquid formulation has a $C_{max}$, $AUC_{inf}$, and/or $AUC_{(0-T)}$ from 80% to 125% of the $C_{max}$, $AUC_{inf}$, and/or $AUC_{(0-T)}$, respectively, of an apixaban oral tablet comprising crystalline apixaban particles having a $D_{90}$ (90% of the volume) as measured by laser light scattering, equal to or less than about 89 μm, and a pharmaceutically acceptable diluent or carrier, as described in U.S. Patent Application Publication No. 2013/0045245, which is herein incorporated by reference in its entirety. Such diluent or carrier may include anhydrous lactose, microcrystalline cellulose, croscarmellose sodium, magnesium stearate, sodium lauryl sulfate, opadry dispersion, or any combination thereof.

In an embodiment of the present invention, a liquid apixaban formulation comprises apixaban and an oral pharmaceutically acceptable liquid vehicle, wherein the formulation is substantially free of apixaban crystals. As used herein in reference to a liquid apixaban formulation, "substantially free of apixaban crystals" means that less than about 10 weight %, including less than 10, 9, 8, 7, 6, 5, 4, 3, 2, 1, 0.5 weight %, and also including 0 weight %, of apixaban present in the formulation is in crystalline form.

Yet another embodiment of the present invention is a method for treating a thromboembolic disorder comprising administering to a patient in need thereof a therapeutically effective amount of a liquid formulation comprising apixaban and a vehicle as described above.

Yet another embodiment of the present invention is a method of administering a pharmaceutical composition, wherein the method comprises administering a dose of the pharmaceutical composition comprising apixaban in an orally acceptable liquid formulation, wherein the dose is less than 30 mL and is administered at least once daily. For example, this dose may be administered twice daily.

The dose may be less than or equal to about 25 mL, less than or equal to about 20 mL, less than or equal to about 15 mL, less than or equal to about 10 mL, less than or equal to about 7.5 mL, less than or equal to about 5 mL, less than or equal to about 3 mL, less than or equal to about 2.5 mL, less than or equal to about 2 mL, less than or equal to about 1 mL, or less than or equal to about 0.5 mL.

The administered composition may comprise from about 0.50 mg to about 5.0 mg of apixaban. This composition may include, for example, about 0.5 mg of apixaban, about 0.75 mg of apixaban, about 1.00 mg of apixaban, about 1.25 mg of apixaban, about 1.50 mg of apixaban, about 1.75 mg of apixaban, about 2.00 mg of apixaban, about 2.25 mg of apixaban, about 2.50 mg of apixaban, about 2.75 mg of apixaban, about 3.00 mg of apixaban, about 3.25 mg of apixaban, about 3.50 mg of apixaban, about 3.75 mg of apixaban, about 4.00 mg of apixaban, about 4.25 mg of apixaban, about 4.50 mg of apixaban, about 4.75 mg of apixaban, and about 5.00 mg of apixaban, or any amount of apixaban in between these values.

Yet another embodiment of the present invention is a liquid formulation comprising apixaban and a vehicle as described above for use in treating a thromboembolic disorder.

Yet another embodiment of the present invention is use of a liquid formulation comprising apixaban and a vehicle as described above in the treatment of a thromboembolic disorder.

Yet another embodiment of the present invention is use of a liquid formulation comprising apixaban and a vehicle as described above in the preparation of a medicament for use in treating a thromboembolic disorder.

Thromboembolic disorders mentioned above include those disclosed in U.S. Pat. No. 6,967,208. Non-limiting examples of thromboembolic disorders are arterial cardiovascular thromboembolic disorders, venous cardiovascular thromboembolic disorders, and thromboembolic disorders in the chambers of the heart. Thromboembolic disorders may also include unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

Specific embodiments of the invention will now be demonstrated by reference to the following examples. It should be understood that these examples are disclosed by way of illustrating the invention and should not be taken in any way to limit the scope of the present invention.

EXAMPLES

TABLE 3

Examples 1-3 and Reference Examples 1-4.

| Component | Ref. Ex. 1 (% w/w) | Ref. Ex. 2 (% w/w) | Ref. Ex. 3 (% w/w) | Ref. Ex. 4 (% w/w) | Ex. 1 (% w/w) | Ex. 2 (% w/w) | Ex. 3 (% w/w) |
|---|---|---|---|---|---|---|---|
| Glycerine | 20.00 | 20.00 | 25.50 | | 20.00 | 20.00 | 19.953 |
| Propylene glycol | 14.00 | 7.00 | 14.00 | 10.00 | 14.00 | 14.00 | 13.967 |
| PEG 400 | 5.00 | 5.00 | 5.00 | 15.00 | 5.00 | 5.00 | 4.988 |
| Polysorbate 80 | 7.00 | 12.50 | 7.00 | 12.50 | 12.50 | 12.50 | 12.471 |
| Povidone K29/32 | 2.50 | 2.50 | 2.50 | | 2.50 | | |
| Povidone K25 | | | | | | 4.00 | 3.991 |
| Sorbitol (70%) | 20.00 | 20.00 | 20.00 | 20.00 | 20.00 | 20.00 | |
| Fructose | | | | | | | 19.953 |
| Sodium lauryl sulfate | 0.50 | 0.50 | 0.50 | 0.25 | 0.50 | 0.50 | |
| Purified Water, USP | 31.00 | 32.5 | 25.50 | 42.25 | 25.50 | 24.00 | 23.944 |
| Benzoic Acid | | | | | | | 0.213 |
| Citric Acid Anhydrous | | | | | | | 0.008 |
| Sodium Citrate Dihydrate | | | | | | | 0.013 |
| Total | 100.00 | 100.00 | 100.00 | 100 | 100.00 | 100.00 | 100.000 |
| Solubility of apixaban (mg/mL) | <0.5 | <0.5 | <0.5 | <0.5 | 0.634 | 0.707 | 0.741 |

Examples 1 and 2 show a vehicle that contains glycerin, propylene glycol, polyethylene glycol 400, polysorbate 80, povidone, sodium laurly sulfate, water, and sorbitol.

Example 3 shows a composition similar to Examples 1 and 2, but with fructose instead of sorbitol. Example 3 provided an even further enhancement in solubility.

Example 4 shows a formulation based on Example 3 and also contains flavor, sweetener, and preservatives, which are added to provide acceptable taste and improved anti-microbial attributes of the formulation. In this formulation, apixaban is dissolved.

Example 4

| Component | % w/w | Quantity (mg/mL) |
|---|---|---|
| Apixaban | 0.034 | 0.40 |
| Glycerin | 19.953 | 235.45 |
| Propylene Glycol | 13.967 | 164.81 |

-continued

| Component | % w/w | Quantity (mg/mL) |
|---|---|---|
| PEG 400 | 4.988 | 58.86 |
| Polysorbate 80 | 12.471 | 147.16 |
| Povidone K25 | 3.991 | 47.09 |
| Sodium Lauryl Sulfate | 0.499 | 5.89 |
| Fructose | 19.953 | 264.20 |
| Citric Acid Anhydrous | 0.0127 | 235.45 |
| Sodium Citrate Dihydrate | 0.0057 | 0.150 |
| Sucralose | 0.400 | 0.067 |
| Orange Flavor, Ungerer #FN924 | 1.250 | 4.72 |
| Methyl Paraben | 0.0770 | 14.75 |
| Propyl Paraben | 0.0085 | 0.909 |
| Purified Water | 22.390 | 0.100 |

Example 5

Palatability

Palatability is an important aspect for a pediatric drug since it directly influences the patient's acceptance of and adherence to treatment. A series of studies were conducted to evaluate the taste attributes of apixaban liquid formulation and to guide formulation development.

Figure 1B:
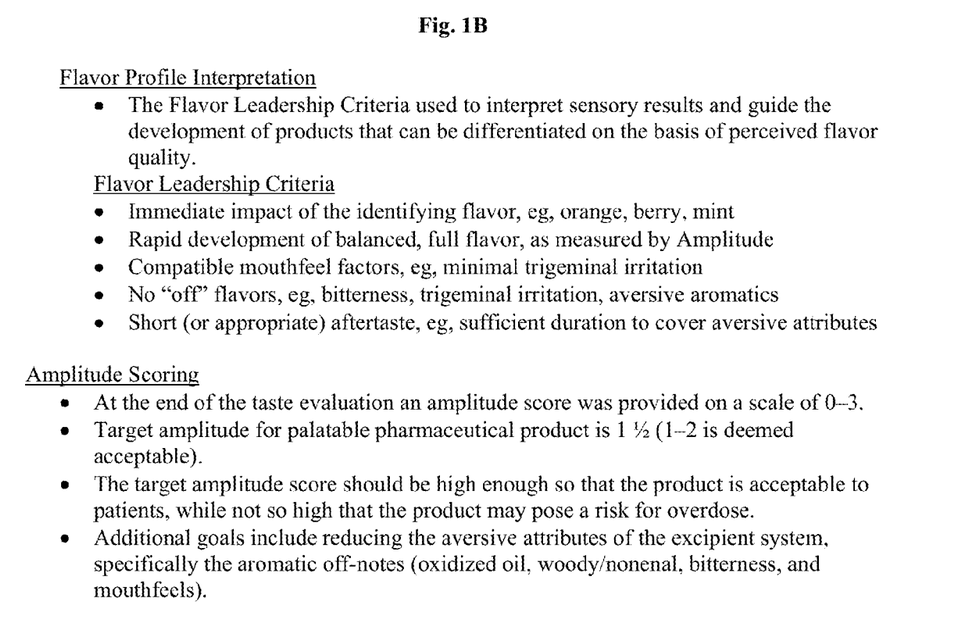

Three taste assessment studies were conducted during the development of a palatable apixaban liquid formulation, and then at 1- and 2-years' post-manufacture to ensure palatability after storage. In each study, formulations were evaluated by four to five professional sensory panelists using the Flavor Profile method of descriptive sensory analysis to identify and quantify taste attributes (such as sweet, aromatic, and sour). Flavor Leadership Criteria were used to interpret flavor profiles and guide taste optimization. Alternative preservative, sweetener, and flavor systems were evaluated and adjusted for the final formulation. The taste assessment method is described in more detail in FIGS. 1A and 1B. Safety assessments were performed throughout the studies.

Figure 2A:
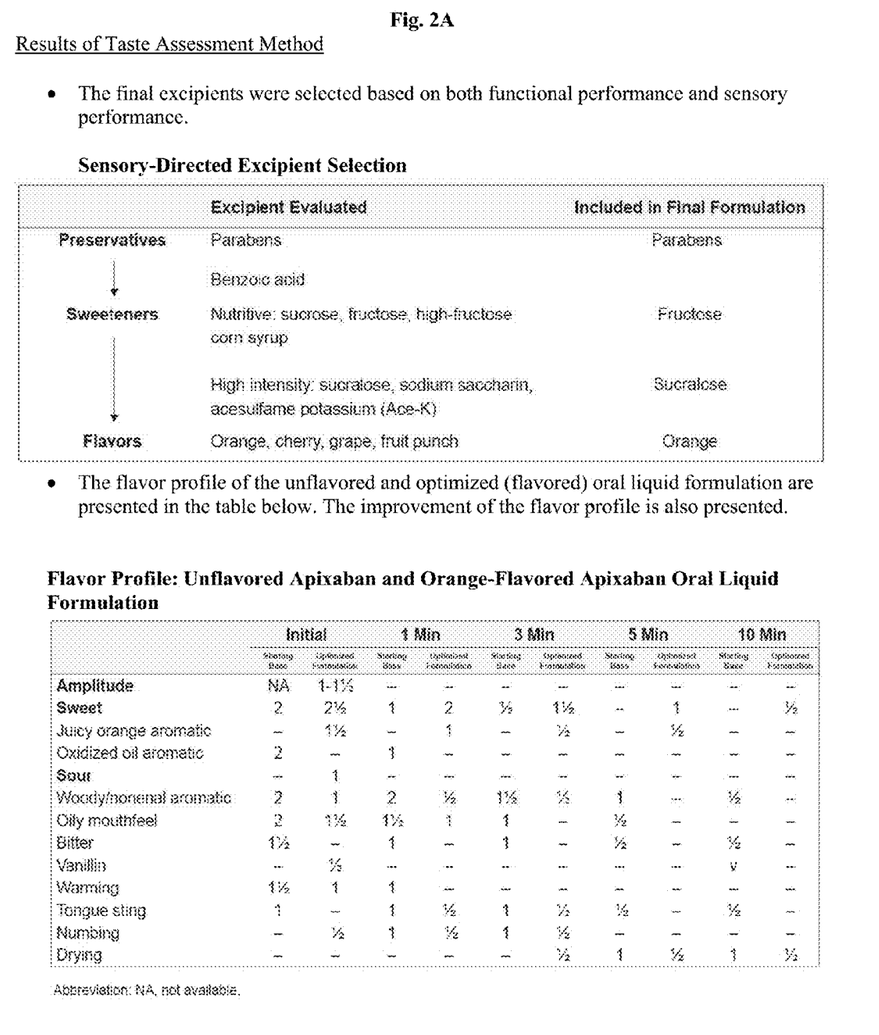
FIGS. 2A and 2B show the results of the taste assessment studies in Example 5.
Figure 2B:
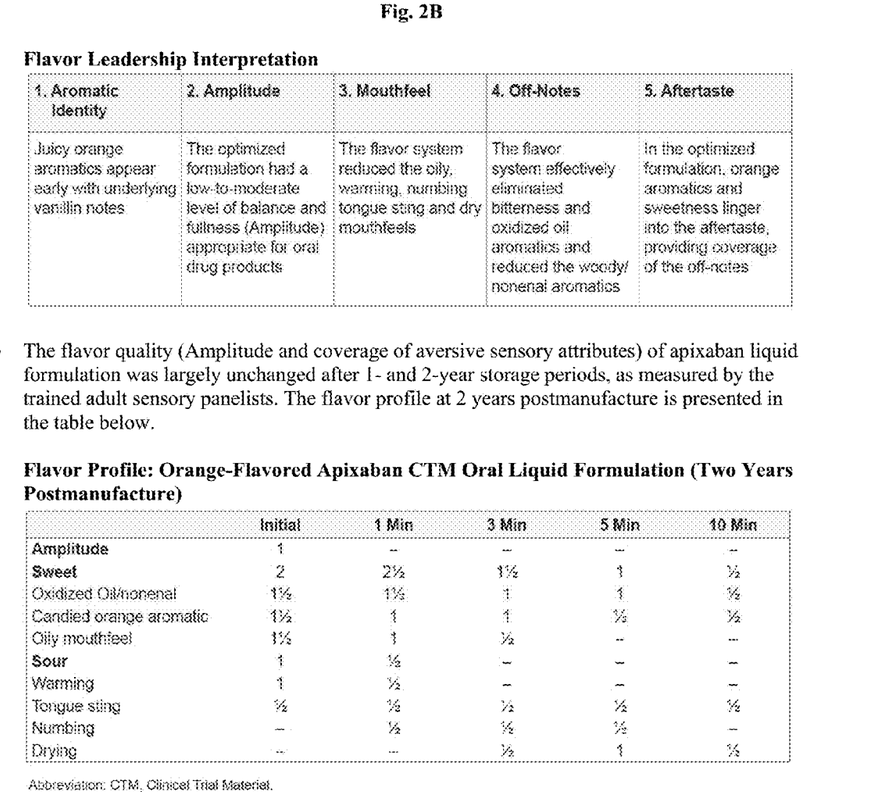

The results of the taste assessment studies are shown in FIGS. 2A and 2B. Amplitude is a measure of overall palatability, and the target for drug products is 1½ (generally 1-2 out of a scale of 0-3) based on historical data of pharmaceutical and consumer products. The amplitude score of the clinical trial batch of apixaban orange-flavored liquid formulation of Example 4 was 1-1½ at the time of manufacture. The score was 1 at 1- and 2-years' post-manufacture, which was acceptable.

Example 6

The relative bioavailability (Frel) of a 0.4 mg/mL apixaban liquid formulation of Example 4 was evaluated via a series of studies. The apixaban liquid formulation was administered orally (PO), via nasogastric tube (NGT) with different flush media, or with an enteral meal (BOOST Plus®). Frel of a crushed tablet administered via NGT versus oral liquid formulation was also evaluated. The tablet comprises crystalline apixaban particles having a $D_{90}$ less than 89 μm, as well as anhydrous lactose, microcrystalline cellulose, croscarmellose sodium, magnesium stearate, sodium lauryl sulfate, and opadry dispersion. The effect of different flush media [D5W and infant formula (Similac®)] and coadministered nutritional supplement (Boost Plus®) on the liquid formulation's bioavailability was assessed.

Three open-label, randomized, crossover studies were conducted. In the first study, which was an open-label, randomized, 2-way crossover study, 14 healthy subjects received apixaban 10 mg as tablet (2×5 mg) and oral liquid formulation (25 mL×0.4 mg/mL). In the second study, which was an open-label, randomized, 3-way crossover study, 21 healthy subjects received apixaban 5 mg as oral liquid formulation (12.5 mL×0.4 mg/mL), via NGT flushed by 60 mL D5W, and via NGT flushed by 60 mL infant formula. In the third study, which was an open-label, randomized, 3-way crossover study, 21 healthy subjects received apixaban 5 mg as oral liquid formulation (12.5 mL×0.4 mg/mL), liquid formulation (12.5 mL×0.4 mg/mL) via NGT with 240 mL BOOST Plus®, and crushed tablet (5 mg) suspended in 60 mL D5W via NGT. Serial pharmacokinetics samples were collected. Point estimates and 90% confidence intervals (CIs) for ratios of geometric means (GMRs) were generated for $C_{max}$, $AUC_{(0-T)}$ and $AUC_{inf}$. Frel was defined as the ratio of $AUC_{infs}$.

In these studies, key inclusion criteria included: (i) healthy subjects, aged 18-45 years, body mass index 18-30 kg/m$^2$, inclusive; no clinically significant deviation from normal in medical history, physical examination electrocardiograms (ECGs), and clinical laboratory determinations; and (ii) women of child-bearing potential had a negative serum pregnancy test within 24 h prior to the start of investigational product. Key exclusion criteria included: (i) any history or evidence of abnormal bleeding or coagulation disorders, intracranial hemorrhage, or abnormal bleeding; (ii) any gastrointestinal surgery that could impact upon the absorption of study drug; and (iii) current or recent (within 3 months) gastrointestinal disease including, but not limited to dyspepsia, gastrointestinal ulcers, esophageal or gastric varices, or hemorrhoids.

For pharmacokinetic assessment, blood samples were collected for assay of apixaban concentration for up to 72 hours post-dose. PK parameters ($C_{max}$, $AUC_{inf}$, $AUC_{(0-T)}$, $T_{max}$, and $T_{1/2}$) were derived from plasma concentration-time profiles of apixaban.

The nutritional contents of the liquid formulations studied are shown in Table 4 below.

TABLE 4

Nutritional contents of the liquid formulations studied
Nutritional Contents

| | Study 2 | | Study 3 |
|---|---|---|---|
| | D5W 60 mL | Similac 60 mL | Boost Plus 240 mL |
| Calories | 12 | 49 | 365 |
| Total fat (g) | | 2 | 14 |
| Saturated Fat (g) | | 2 | 2 |
| Trans Fat (g) | | 0 | 0 |
| Total Carbohydrate (g) | | 6 | 46 |
| Dietary fiber (g) | | 0 | 3 |
| Sugars (g) | 3 | 6 | 24 |
| Protein (g) | | 2 | 14 |
| Cholesterol (mg) | | 2 | 10 |
| Sodium (mg) | | 20 | 203 |

Figure 3:
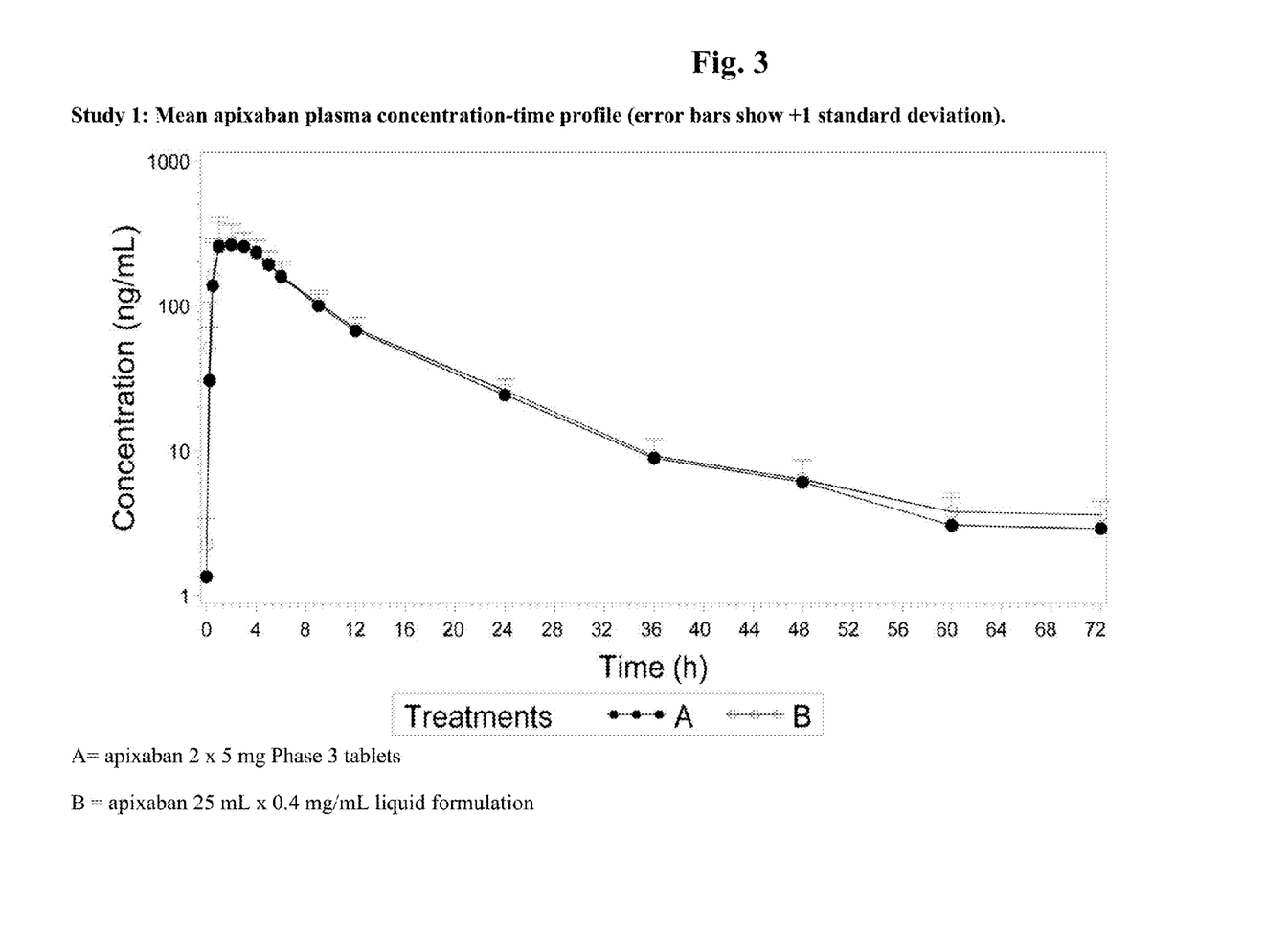
FIG. 3 is a mean apixaban plasma concentration-time profile (error bars show +1 standard deviation) of (A) an apixaban tablet and (B) an apixaban oral liquid formulation of an embodiment of the present invention (Study 1).

In the first study (Study 1), apixaban mean $C_{max}$ and AUC were similar for the two treatments, namely, oral liquid formulation and tablet, as shown in the tables below. Median $T_{max}$ was 2 h for the two treatments. Apixaban mean $T_{1/2}$ was similar for the 2 treatments (12.3 and 13.8 h) as seen in FIG. 3. Relative bioavailability of apixaban liquid formulation versus tablet was 105%.

TABLE 5

Apixaban plasma pharmacokinetic parameters

| Treatment | $C_{max}$ (ng · h/mL) Geo. Mean (% CV) | $T_{max}$ (h) Median (Min-Max) | $AUC_{(0-T)}$ (ng · h/mL) Geo. Mean (% CV) | $AUC_{inf}$ (ng · h/mL) Geo. Mean (% CV) | $T_{1/2}$ (h) Mean (SD) | Frel (%) |
|---|---|---|---|---|---|---|
| A (N = 13)* | 294 (37) | 2.00 (0.50-4.05) | 2663 (22) | 2707 (21) | 12.3 (4.53) | B vs. A 105 |
| B (N = 13)* | 287 (30) | 2.00 (1.00-4.00) | 2790 (21) | 2855 (21) | 13.8 (6.09) | |

N = 14 for Treatment A: $C_{max}$ and $T_{max}$
Geo. = Geometric
A = Apixaban 2 × 5 mg Phase 3 tablets
B = Apixaban 25 mL × 0.4 mg/mL liquid formulation

TABLE 6

Statistical analysis of apixaban plasma pharmacokinetic parameters

| Treatment and Comparison | $C_{max}$ (ng · h/mL) Adj. Geo. Mean | $AUC_{inf}$ (ng · h/mL) Adj. Geo. Mean (CV) | $AUC_{(0-T)}$ (ng · h/mL) Adj. Geo. Mean (CV) |
|---|---|---|---|
| A | 293.99 | 2712.48 | 2668.31 |
| B | 287.43 | 2848.97 | 2784.37 |
| B vs. A | AGM(90% CI) 0.977(0.756, 1.261) | AGM(90% CI) 1.050(0.938, 1.176) | AGM(90% CI) 1.043(0.933, 1.167) |

Figure 4:
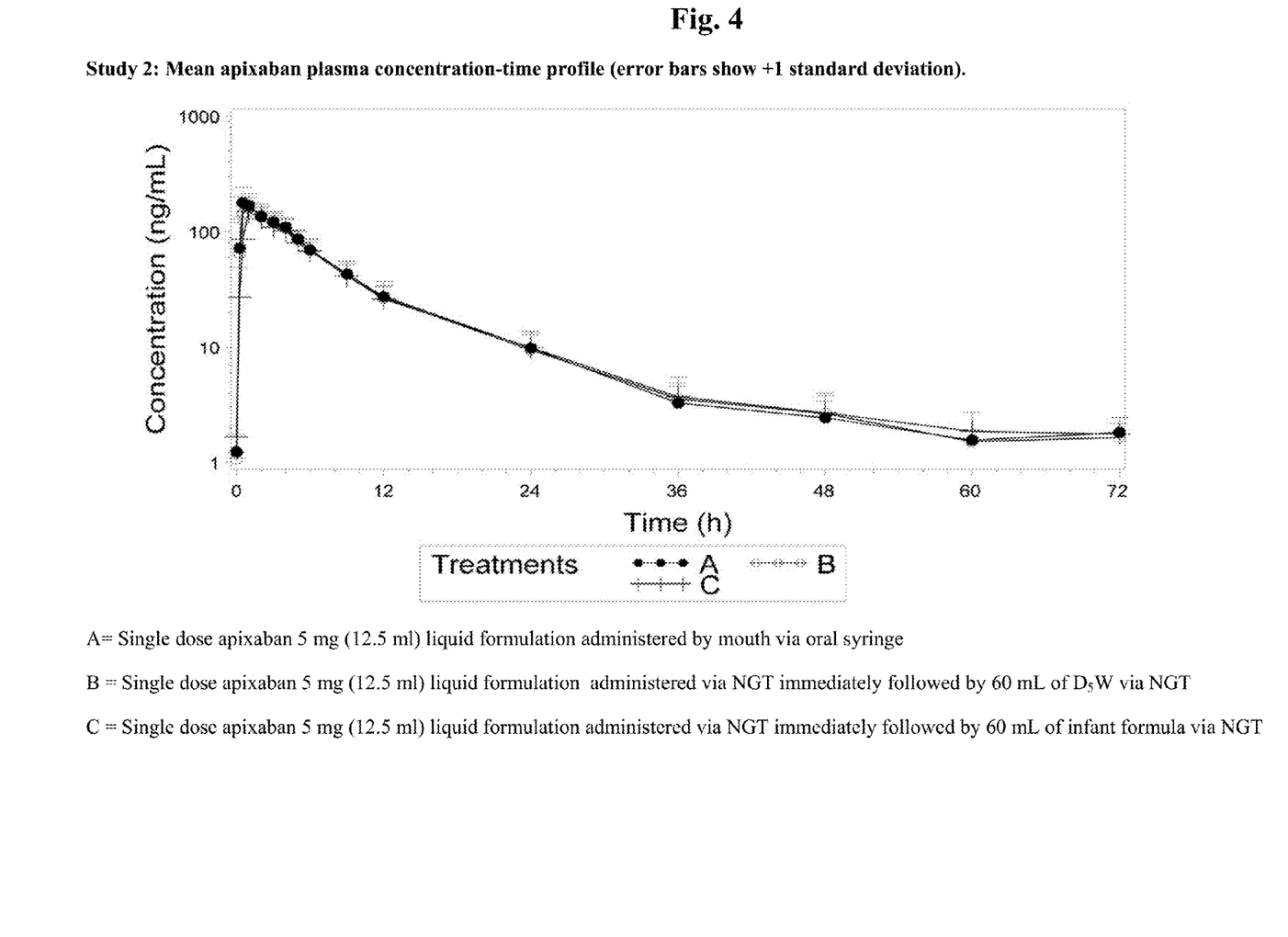
FIG. 4 is a mean apixaban plasma concentration-time profile of an apixaban oral liquid formulation of an embodiment of the present invention administered (A) by mouth via oral syringe, (B) via NGT immediately followed by 60 mL of D5W via NGT, and (C) via NGT immediately followed by 60 mL of infant formula via NGT (Study 2).

In the second study (Study 2), apixaban median $T_{max}$ was 0.5-1 h across the 3 treatments, namely, oral liquid formulation, via NGT flushed by 60 mL D5W, and via NGT flushed by 60 mL infant formula, as shown in table below. Apixaban mean $T_{1/2}$ was similar across the 3 treatments (~10.5 h) as seen in FIG. 4. Administration of apixaban liquid formulation via NGT and flushed with 60 mL of D5W resulted in comparable bioavailability to oral administration of the liquid formulation as seen in tables below (Frel was 96.7%). When apixaban 5 mg liquid formulation was administered through an NGT and flushed with 60 mL of infant formula, the geometric means for $C_{max}$, $AUC_{inf}$ and $AUC_{(0-T)}$ of apixaban were 19%, 8% and 8% lower, respectively, relative to those observed following oral administration of apixaban 5 mg liquid formulation as seen in tables below (Frel was 92.2%).

TABLE 8

Statistical analysis of apixaban plasma pharmacokinetic parameters

| Treatment and Comparison | $C_{max}$ (ng · h/mL) Adj. Geo. Mean | $AUC_{inf}$ (ng · h/mL) Adj. Geo. Mean (CV) | $AUC_{(0-T)}$ (ng · h/mL) Adj. Geo. Mean (CV) |
|---|---|---|---|
| A | 191 | 1293 | 1270 |
| B | 182 | 1251 | 1226 |
| C | 154 | 1192 | 1167 |

| | Ratio of Adjusted Geometric Means (90% CI) | | |
|---|---|---|---|
| B vs. A | 0.953 (0.873, 1.040) | AGM (90% CI) 0.922 (0.899, 0.947) | AGM (90% CI) 0.919 (0.896, 0.942) |
| C vs. A | 0.805 (0.749, 0.865) | | |

Figure 5:
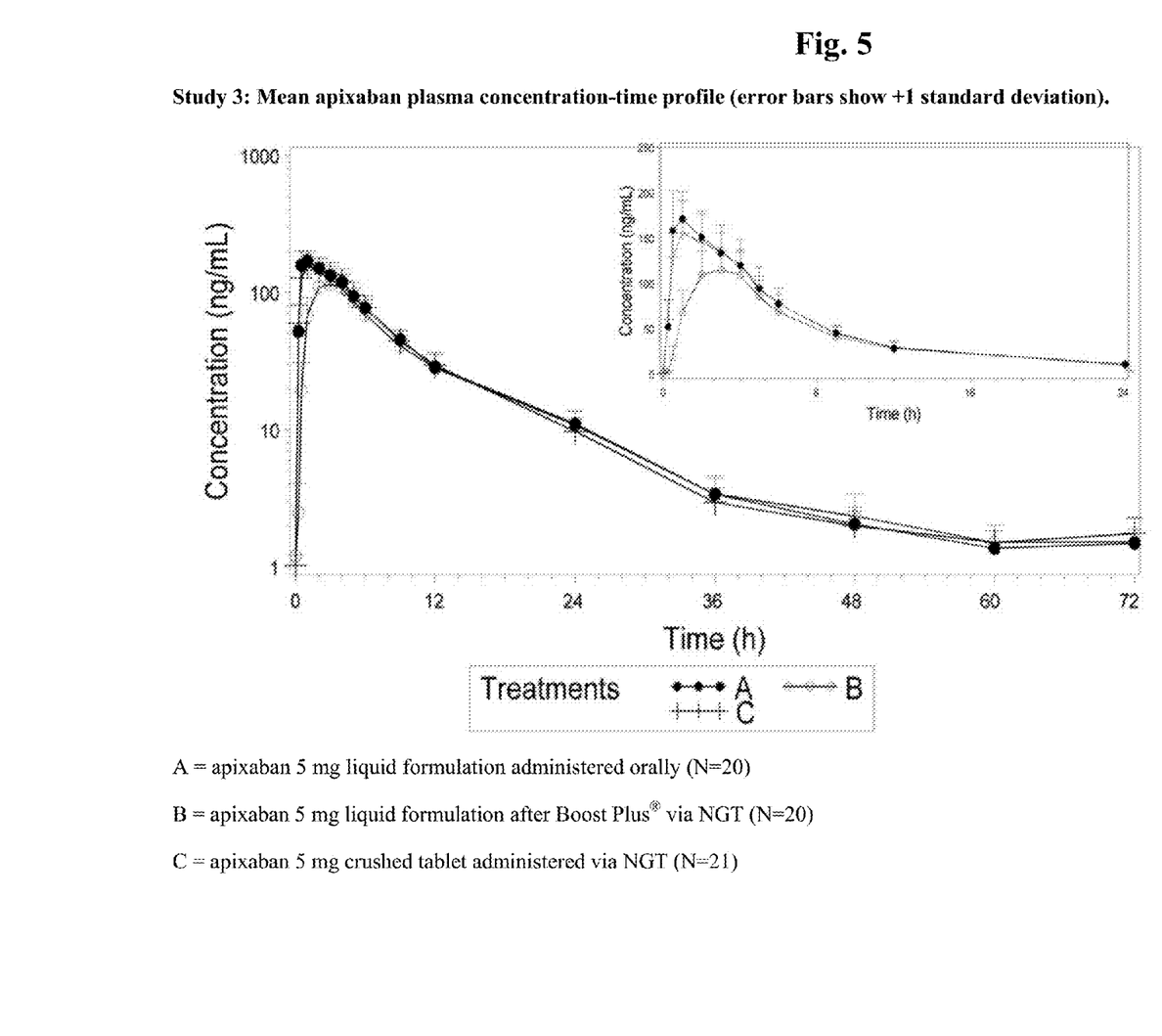
FIG. 5 is a mean apixaban plasma concentration-time profile (error bars show +1 standard deviation) of an apixaban oral liquid formulation of an embodiment of the present invention administered (A) orally, (B) after Boost Plus, and (C) a crushed apixaban tablet administered via NGT (Study 3).

In the third study (Study 3), apixaban mean $C_{max}$ and AUC were similar between the liquid formulation oral administration and crushed tablet, while Boost Plus through NGT had 32% and 19% lower $C_{max}$ and AUC as seen in the tables below. Median $T_{max}$ was 1 h for the oral liquid formulation administration and crushed tablet through NGT, while $T_{max}$ was 3 hr for liquid formulation through NGT in the presence of Boost Plus. Apixaban mean $T_{1/2}$ was similar between the 3 treatments (9.6-11.2 h) as seen in FIG. 5. When 5 mg (12.5 mL) of apixaban oral liquid formulation was administered through an NGT in the presence of a liquid meal challenge, Boost Plus®, apixaban $C_{max}$, $AUC_{inf}$ and $AUC_{(0-T)}$ were 32%, 19%, and 19% lower, respectively, relative to those observed following administration of apixaban oral liquid formulation via oral syringe. When a 5 mg

TABLE 7

Apixaban plasma pharmacokinetic parameters

| Treatment | $C_{max}$ (ng · h/mL) Geo. Mean (CV) | $AUC_{(0-T)}$ (ng · h/mL) Geo. Mean (CV) | $AUC_{inf}$ (ng · h/mL) Geo. Mean (CV) | $T_{max}$ (h) Median (Min-Max) | $T_{1/2}$ (h) Mean (SD) | Frel Geo. Mean (% CV) |
|---|---|---|---|---|---|---|
| A (N = 21) | 189 (23) | 1257 (21) | 1280 (21) | 0.517 (0.48-2.00) | 10.5 (4.2) | N/A |
| B (N = 21) | 180 (22) | 1214 (26) | 1239 (25) | 1.000 (0.30-2.00) | 10.4 (4.5) | 0.967 (11) |
| C (N = 21) | 153 (20) | 1154 (26) | 1181 (26) | 1.00 (0.48-2.00) | 10.6 (3.8) | 0.922 (7) |

A = Single dose apixaban 5 mg (12.5 mL) administered by mouth via oral syringe
B = Single dose apixaban 5 mg (12.5 mL) administered via NGT immediately followed by 60 mL of D5W via NGT
C = Single dose apixaban 5 mg (12.5 mL) administered via NGT immediately followed by 60 mL of infant formula via NGT apixaban crushed tablet was administered through an NGT suspended in 60 mL D5W, the 90% CIs for the estimated geometric mean ratios for $C_{max}$, $AUC_{inf}$ and $AUC_{(0-T)}$ fell entirely within the predefined bioequivalence interval (0.80-1.25).

TABLE 9

Summary Statistics of Apixaban Pharmacokinetic Parameters

| Treatment | $C_{max}$ (ng · h/mL) Geo. Mean (% CV) | $AUC_{inf}$ (ng · h/mL) Geo. Mean (% CV) | $AUC_{(0-T)}$ (ng · h/mL) Geo. Mean (% CV) | $T_{max}$ (h) Median (Min-Max) | $T_{1/2}$ (h) Mean (SD) | Frel Geo. Mean (% CV) |
|---|---|---|---|---|---|---|
| TRT A (n = 20) | 177 (19) | 1380 (15) | 1354 (15) | 1.00 (0.5-2.0) | 11.21 (6.903) | |
| TRT B (n = 20) | 121 (21) | 1122 (18) | 1098 (18) | 3.00 (1.0-4.2) | 9.56 (2.424) | 0.813 (16) |
| TRT C (n = 21) | 158 (22) | 1321(18) | 1295 (18) | 1.00 (0.5-3.0) | 10.40 (7.835) | 0.951 (13)[a] |

TRT A = Apixaban 5 mg oral liquid formulation (0.4 mg/mL × 12.5 mL) administered orally
TRT B = Apixaban 5 mg oral liquid formulation (0.4 mg/mL × 12.5 mL) after Boost Plus ® via NGT
TRT C = Apixaban 5 mg crushed tablet via NGT
Note:
A subject discontinued in Period 1 under Treatment C.
[a]n = 20

TABLE 10

Statistical Analysis of Apixaban $C_{max}$, $AUC_{(INF)}$, and $AUC_{(0-T)}$

| Treatment and Comparison | $C_{max}$ (ng · h/mL) Adj. Geo. Mean | $AUC_{inf}$ (ng · h/mL) Adj. Geo. Mean (CV) | $AUC_{(0-T)}$ (ng · h/mL) Adj. Geo. Mean (CV) |
|---|---|---|---|
| TRT A | 179 | 1398 | 1373 |
| TRT B | 122 | 1136 | 1112 |
| TRT C | 158 | 1327 | 1301[a] |

| | Ratio of Adjusted Geometric Means (90% CI) | | |
|---|---|---|---|
| TRT B vs. TRT A | 0.682 (0.621, 0.748) | 0.813 (0.766, 0.863) | 0.810 (0.764, 0.860) |
| TRT C vs. TRT A | 0.884 (0.830, 0.942) | 0.950 (0.905, 0.997) | 0.947 (0.903, 0.994) |

TRT A = Apixaban 5 mg oral liquid formulation (0.4 mg/mL × 12.5 mL) administered orally
TRT B = Apixaban 5 mg oral liquid formulation (0.4 mg/mL × 12.5 mL) after Boost Plus ® via NGT
TRT C = Apixaban 5 mg crushed tablet via NGT
Note:
A subject discontinued in Period 1 under Treatment C.
[a]n = 20

Frel for liquid formulation versus tablet was 105%. Frel for liquid formulation with D5W flush, with infant formula flush, with BOOST Plus®, and crushed tablet versus oral liquid formulation was 97%, 92%, 81%, and 95%, respectively. The GMR and 90% CI met bioequivalence (BE) criteria for all AUCs except BOOST Plus® (0.813 [0.766, 0.863]). The GMR and 90% CI for each $C_{max}$ met BE criteria except for liquid formulation versus tablet (0.977 [0.756, 1.261]); or versus oral liquid formulation for liquid formulation via NGT infant formula flush (0.805 [0.749, 0.865]), and liquid formulation via NGT with BOOST Plus® (0.682 [0.621, 0.748]). Each $T_{max}$ was comparable for all treatments (median 0.5-2 hr) except BOOST Plus® ($T_{max}$=3 hr). Thus, comparable Frel was observed between oral apixaban liquid formulation and tablet, and between oral liquid formulation and NGT administration of liquid formulation flushed with D5W and infant formula, or crushed tablet. Administration of the liquid formulation via NGT with BOOST Plus® resulted in 19% lower exposure than that obtained following fasted oral apixaban liquid formulation administration.

Safety assessments were made based on adverse event reports and the results of vital sign measurements, ECGs, physical examinations, and clinical laboratory tests. It was found that apixaban was safe and well tolerated by subjects in the studies.

Example 7

Apixaban solution at a dose of 0.21 mg/m² is administered by mouth or by nasogastric tube (NG) or gastronomy tube (G-tube) using a dosing syringe on the morning of Day 1 to neonates up to 27 days of age.

Example 8

Apixaban solution at a dose of 1.08 mg/m² is administered by mouth or by nasogastric tube (NG) or gastronomy tube (G-tube) using a dosing syringe on the morning of Day 1 to subjects in the age group ≥28 days to <2 years.

Example 9

Apixaban solution at a dose of 1.17 mg/m² is administered by mouth or by nasogastric tube (NG) or gastronomy tube (G-tube) using a dosing syringe on the morning of Day 1 to subjects in the age group 2 years to <6 years.

Example 10

Apixaban solution at a dose of 1.80 mg/m² is administered by mouth or by nasogastric tube (NG) or gastronomy tube (G-tube) using a dosing syringe on the morning of Day 1 to subjects in the age group 6 years to <12 years.

Example 11

Apixaban solution at a dose of 2.19 mg/m² is administered by mouth or by nasogastric tube (NG) or gastronomy tube (G-tube) using a dosing syringe on the morning of Day 1 to subjects in the age group 12 years to <18 years.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

The invention claimed is:

1. A liquid formulation comprising apixaban and a vehicle, wherein:
   water content of the vehicle is about 20% to about 30% w/w of the vehicle; non-ionic surfactant content of the vehicle is about 11% to about 14% w/w of the vehicle;
   ionic surfactant content of the vehicle is about 0.2% to about 1% w/w of the vehicle;
   hydrophilic polymer content of the vehicle is about 1% to about 6% w/w of the vehicle;
   polyhydric alcohol content of the vehicle is about 31% to about 37% w/w of the vehicle;
   polyethylene glycol content of the vehicle is about 4% to about 6% w/w of the vehicle; and
   carbohydrate content of the vehicle is about 18% to about 22% w/w of the vehicle;
   wherein a solubility of apixaban in the vehicle is at least 0.50 mg/mL.

2. The liquid formulation of claim 1, wherein the solubility of apixaban in the vehicle is at least 0.60 mg/mL.

3. The liquid formulation of claim 1, wherein the solubility of apixaban in the vehicle is about 0.70 mg/mL to about 0.74 mg/mL.

4. The liquid formulation of claim 1, wherein:
   the water content of the vehicle is about 23% to about 27% w/w of the vehicle;
   the non-ionic surfactant content of the vehicle is about 11.5% to about 13.5% w/w of the vehicle;
   the ionic surfactant content of the vehicle is about 0.2% to about 0.8% w/w of the vehicle;
   the hydrophilic polymer content of the vehicle is about 2% to about 5% w/w of the vehicle;
   the polyhydric alcohol content of the vehicle is about 32% to about 36% w/w of the vehicle;
   the polyethylene glycol content of the vehicle is about 4.5% to about 5.5% w/w of the vehicle; and
   the carbohydrate content of the vehicle is about 19% to about 21% w/w of the vehicle.

5. The liquid formulation of claim 1, wherein:
   the water content of the vehicle is about 23.5% to about 26% w/w of the vehicle;
   the non-ionic surfactant content of the vehicle is about 12% to about 13% w/w of the vehicle;
   the ionic surfactant content of the vehicle is about 0.4% to about 0.6% w/w;
   the hydrophilic polymer content of the vehicle is about 2.2% to about 4.2% w/w of the vehicle;
   the polyhydric alcohol content of the vehicle is about 33% to about 35% w/w of the vehicle;
   the polyethylene glycol content of the vehicle is about 4.8% to about 5.2% w/w of the vehicle; and
   the carbohydrate content of the vehicle is about 19.8% to about 20.2% w/w.

6. The liquid formulation of claim 1, comprising at least one of:
   glycerin,
   propylene glycol,
   polyethylene glycol,
   polysorbate,
   povidone,
   sorbitol,
   sodium lauryl sulfate,
   copovidone,
   poloxamer,
   fructose, and
   sucrose.

7. A liquid formulation comprising apixaban and a vehicle, wherein the vehicle comprises:
   water;
   glycerin, at about 15% to about 25% w/w of the vehicle;
   propylene glycol, at about 7% to about 20% w/w of the vehicle;
   polyethylene glycol, at about 2% to about 7% w/w of the vehicle;
   polysorbate, at about 5% to about 18% w/w of the vehicle;
   povidone, at about 2% to about 5% w/w of the vehicle;
   sorbitol, at about 15% to about 25% w/w of the vehicle;
   sodium lauryl sulfate, at about 0.25% to about 1% w/w of the vehicle;
   copovidone, at about 2% to about 5% w/w of the vehicle;
   poloxamer, at about 2% to about 7% w/w of the vehicle;
   fructose, at about 15% to about 25% w/w of the vehicle; and
   sucrose, at about 15% to about 25% w/w of the vehicle.

8. The liquid formulation of claim 1, wherein the vehicle comprises a non-ionic surfactant selected from the group consisting of polyoxyethylene sorbitan fatty acid ester, poloxamer, polyoxyethylene castor oil derivative, polyoxyglyceride, vitamin E polyethylene glycol succinate, and macrogol 15 hydroxystearate.

9. The liquid formulation of claim 1, wherein the vehicle comprises an ionic surfactant selected from the group consisting of sodium lauryl sulfate and docusate sodium.

10. The liquid formulation of claim 1, wherein the vehicle comprises a hydrophilic polymer selected from the group consisting of povidone and copovidone.

11. The liquid formulation of claim 1, wherein the vehicle comprises a polyhydric alcohol selected from the group consisting of glycerin, propylene glycol, sorbitol, and mannitol.

12. The liquid formulation of claim 1, wherein the vehicle comprises a carbohydrate selected from the group consisting of fructose and sucrose.

13. The liquid formulation of claim 1 that is suitable for oral administration.

14. The liquid formulation of claim 1 that is suitable for administration through a nasogastric tube.

15. The liquid formulation of claim 1, wherein the formulation is substantially free of apixaban crystals.

* * * * *

UNITED STATES PATENT AND TRADEMARK OFFICE
CERTIFICATE OF CORRECTION

PATENT NO. : 9,452,134 B2  
APPLICATION NO. : 14/430275  
DATED : September 27, 2016  
INVENTOR(S) : Sherif Ibrahim Farag Badawy et al.

It is certified that error appears in the above-identified patent and that said Letters Patent is hereby corrected as shown below:

On the Title Page

[71] Applicant, add --; Pfizer Inc., New York, NY (US)--.

In the Claims

Column 15:
Line 9, "vehicle; ionic" should read --vehicle;
                              non-ionic--;
Line 49, "0.6% w/w." should read --0.6% w/w of the vehicle.--; and
Line 57, "20.2% w/w." should read --20.2% w/w of the vehicle.--.

Signed and Sealed this
Third Day of October, 2017

Joseph Matal
*Performing the Functions and Duties of the*
*Under Secretary of Commerce for Intellectual Property and*
*Director of the United States Patent and Trademark Office*